(12) United States Patent
Hakala et al.

(10) Patent No.: US 12,109,434 B2
(45) Date of Patent: Oct. 8, 2024

(54) NEURAL NETWORK CALIBRATION FOR RADIOTHERAPY

(71) Applicant: Siemens Healthineers International AG, Steinhausen (CH)

(72) Inventors: Mikko Hakala, Rajamaki (FI); Esa Kuusela, Espoo (FI); Elena Czeizler, Helsinki (FI); Shahab Basiri, Siuntio (FI)

(73) Assignee: Siemens Healthineers International AG, Steinhausen (CH)

( * ) Notice: Subject to any disclaimer, the term of this patent is extended or adjusted under 35 U.S.C. 154(b) by 0 days.

(21) Appl. No.: 18/527,066

(22) Filed: Dec. 1, 2023

(65) Prior Publication Data

US 2024/0115883 A1    Apr. 11, 2024

Related U.S. Application Data

(63) Continuation of application No. 18/114,826, filed on Feb. 27, 2023, now Pat. No. 11,865,369, which is a continuation of application No. 17/124,223, filed on Dec. 16, 2020, now Pat. No. 11,590,367.

(51) Int. Cl.
| | |
|---|---|
| *A61N 5/10* | (2006.01) |
| *G06N 3/045* | (2023.01) |
| *G06N 3/08* | (2023.01) |
| *G06N 20/00* | (2019.01) |

(52) U.S. Cl.
CPC ............ *A61N 5/1064* (2013.01); *G06N 3/045* (2023.01); *G06N 3/08* (2013.01); *G06N 20/00* (2019.01)

(58) Field of Classification Search
CPC ...... A61N 5/1064; G06N 3/0454; G06N 3/08; G06N 20/00; G16H 20/40
See application file for complete search history.

(56) References Cited

U.S. PATENT DOCUMENTS

| | | |
|---|---|---|
| 2010/0317967 A1 | 12/2010 | Carlsen et al. |
| 2019/0333623 A1 | 10/2019 | Hibbard |

OTHER PUBLICATIONS

Guo et al., "On Calibration of Modern Neural Networks," (2017), arXiv: 1706.04599v2 [cs.LG] (14 pages).
International Search Report and Written Opinion for PCT Appl. Ser. No. PCT/EP2021/085838 dated Mar. 23, 2022 (12 pages).

(Continued)

*Primary Examiner* — Mark R Gaworecki
(74) *Attorney, Agent, or Firm* — FOLEY & LARDNER LLP

(57) ABSTRACT

Disclosed herein are systems and methods for identifying radiation therapy treatment data for patients. A processor accesses a neural network trained based on a first set of data generated from characteristic values of a first set of patients that received treatment at one or more first radiotherapy machines. The processor executes the neural network using a second set of data comprising characteristic values of a second set of patients receiving treatment at one or more second radiotherapy machines. The processor executes a calibration model using an output of the neural network based on the second set of data to output a calibration value. The processor executes the neural network using a set of characteristics of a first patient to output a first confidence score associated with a first treatment attribute. The processor then adjusts the first confidence score according to the calibration value to predict the first treatment attribute.

20 Claims, 4 Drawing Sheets

(56) References Cited

OTHER PUBLICATIONS

Non-Final Office Action on U.S. Appl. No. 18/114,826 dated Jul. 12, 2023 (6 pages).
Notice of Allowance on U.S. Appl. No. 17/124,223 dated Oct. 26, 2022 (11 pages).
Notice of Allowance on U.S. Appl. No. 18/114,826 dated Sep. 20, 2023 (8 pages).

NEURAL NETWORK CALIBRATION FOR RADIOTHERAPY

CROSS-REFERENCE TO RELATED APPLICATIONS

This application is a continuation of U.S. patent application Ser. No. 18/114,826, filed Feb. 27, 2023, which is a continuation of U.S. patent application Ser. No. 17/124,223, filed Dec. 16, 2020, each of which is incorporated by reference herein in its entirety for all purposes.

TECHNICAL FIELD

This application relates generally to calibrating an externally trained neural network model to a data distribution of patients being treated at a set of radiotherapy machines.

BACKGROUND

Radiation therapy treatment planning (RTTP) is a complex process that contains specific guidelines, protocols and instructions adopted by different medical professionals, such as clinicians, medical device manufacturers, treating physicians, and the like. Due to the extreme nature of radiation emitted from radiotherapy machines, it is imperative that all the instructions are precisely followed. Field Geometry, as used in the context of RTTP, refers to various attributes or settings of a radiotherapy machine while a patient receives a prescribed radiotherapy dose. For instance, a prescribing physician may identify a source location (e.g., patient's organ to be treated or tumor to be eradicated) and a corresponding dosage. Moreover, other parties (e.g., clinicians or machine manufacturers) may determine positioning attributes (e.g., angles) of the gantry and the patient on the couch to provide optimum treatment.

Conventionally, identifying and applying guidelines to implement radiation therapy treatment are performed by the clinician/technician. For instance, selecting the most suitable field geometry for a patient is one aspect of RTTP that has been delegated to clinicians who use their subjective understanding and skill in conjunctions with various external and internal guidelines to identify optimum field geometry for each patient. However, this conventional method may be inefficient.

For instance, as the first step of the field geometry selection, treating physicians may identify the treatment modality (e.g., choose between the volumetric modulated arc therapy (VMAT) or intensity-modulated radiation therapy (IMRT)). Treating physicians may then decide whether a coplanar or non-coplanar treatment is preferred. Treating physicians may then determine beam limiting device angles for the treatment. In the case of IMRT, the beam delivery directions and number of beams are the specifically relevant variables that must be decided, whereas for VMAT, the technician may need to choose the number of arcs and their corresponding start and stop angles. For these decisions, each provider clinic and/or technician may have his or her own preferences and practices. For instance, a technician may prefer to place the radiation isocenter directly onto the subject area (e.g., tumor) and have a full arc of gantry motion around the subject area. Another technician may approach the same RTTP by having a few fixed field directions and attempt to avoid other organs. Therefore, the same RTTP may be interpreted in different ways, which has produced undesirable results.

SUMMARY

For the aforementioned reasons, there is a desire for a system that can adapt a computer model (e.g., a machine learning model) to predict treatments for patients that are treated at individual sets of radiotherapy machines (e.g., patients that are being treated at individual radiotherapy clinics or patients that are treated in a particular geographical region). Such sets of radiotherapy machines may be used to treat different population distributions and/or be used by clinicians with different treatment outlooks. It may be difficult to generate models that account for these differences given the lack of training data that is typically available from patients that are treated at individual sets of radiotherapy machines (e.g., at individual radiotherapy clinics).

To account for these problems, it is desirable to train a machine learning model using patient data from patients that are treated at different sets of radiotherapy machines (e.g., using training data from multiple radiotherapy clinics where more training data may be available). Once the machine learning model is adequately trained, a provider (e.g., a clinic or a set of clinics) of a particular set of radiotherapy machines that implements the systems and methods described herein may use a processor to access and calibrate the machine learning model to make treatment predictions for patients being treated at the set of radiotherapy machines. Consequently, the provider may use a partially trained machine learning model to accurately predict RTTP predictions such that calculating field geometry (or other radiation therapy treatment attributes) may be tuned to patients being treated by the radiotherapy machines that are managed by the provider. The provider may do so without training the model using training data generated from patients that were treated at the provider's radiotherapy machines, which is often unavailable or too expensive to create.

In one embodiment, a method comprises accessing, by one or more processors, a neural network trained based on a first set of data generated from characteristic values of a first set of patients that received treatment at a set of one or more first radiotherapy machines; executing, by the one or more processors, the neural network using a second set of data comprising characteristic values of a second set of patients receiving treatment at a set of one or more second radiotherapy machines to output a set of treatment attribute predictions, the second set of data having corresponding labels indicating expected treatment attribute predictions; executing, by the one or more processors, a calibration model using the set of treatment attribute predictions and labels indicating expected treatment attribute predictions to output a calibration value; executing, by the one or more processors, the neural network using a set of characteristics of a first patient of the second set of patients receiving treatment at the set of one or more second radiotherapy machines to output a first confidence score associated with a first treatment attribute; and adjusting, by the one or more processors, the first confidence score according to the calibration value to predict the first treatment attribute.

In another embodiment, a system comprises a processor in communication with a radiotherapy machine, the processor configured to execute instructions to: access a neural network trained based on a first set of data generated from characteristic values of a first set of patients that received treatment at a set of one or more first radiotherapy machines; execute the neural network using a second set of data comprising characteristic values of a second set of patients receiving treatment at a set of one or more second radiotherapy machines to output a set of treatment attribute predictions, the second set of data having corresponding labels indicating expected treatment attribute predictions; execute a calibration model using the set of treatment attribute predictions and labels indicating expected treatment attribute predictions to output a calibration value; execute the neural network using a set of characteristics of a first patient of the second set of patients receiving treatment at the set of one or more second radiotherapy machines to output a first confidence score associated with a first treatment attribute; and adjust the first confidence score according to the calibration value to predict the first treatment attribute.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1:
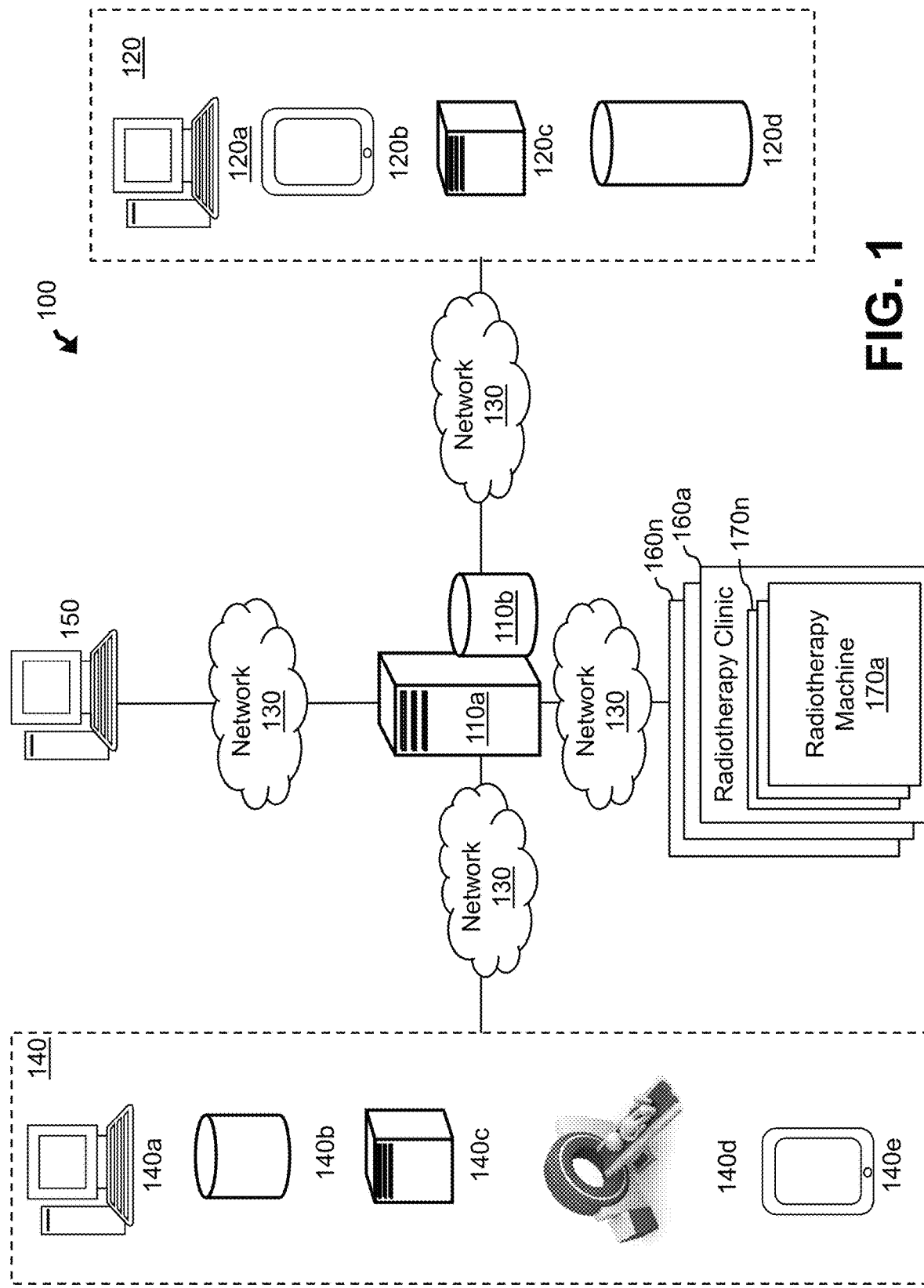
FIG. 1 illustrates components of a treatment attribute identification system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Radiation therapy treatment planning (RTTP) may utilize neural network models (or other machine learning models). For example, neural networks may be used in automatic organ and tumor segmentation. Neural networks may also provide decision support by, for example, suggesting treatment modalities or for selecting more detailed aspects of the treatment, such as determining field geometry settings in external beam radiotherapy. Generally, the main outcome of neural network classifiers is a predicted label for a given unseen case. However, in a clinical setting, in addition to the prediction accuracy (e.g., overall expectation of correctly predicting labels), it may be important for a user to have access to the confidence level of individual predictions so the user can determine whether to use the prediction or to explore other options. Furthermore, it is important to avoid using overconfident or inaccurate predictions to adjust how radiotherapy machines provide treatment. Therefore, it is important for the confidence level to be accurate.

Moreover, in a non-limiting example, when a neural network model is transferred from one clinical or non-clinical context to another, both the prediction accuracy and the confidence of the predictions may be affected. For instance, the distribution of data (population, treatment types, protocols and practices, etc.) at individual clinics may be different from each other, causing processors associated with the clinics to determine different treatments for patients. Consequently, neural networks may need to be trained to predict treatment plans for patients that are treated at individual clinics or at specific radiotherapy machines. One approach to such training could be to retrain a neural network model using site-specific patient data. However, given the amount of training data that is typically required to train a neural network, not all clinics may have the ability or resources to go through the development cycle to tailor their model to patients that use the clinic's radiotherapy machines.

By implementing the systems and methods described herein, a system may resolve these training deficiencies by enabling an externally trained neural network (e.g., a neural network model trained by another processor) to be used to predict RTTP attributes (e.g., treatment attributes) for patients being treated at a set of radiotherapy machines in a certain context (e.g., at a local clinic). The system may do so by calibrating predictions made by the externally trained neural network model to avoid the need to generate site-specific training data for a neural network model. The systems and methods provide for a post-processing calibration procedure to calibrate confidence scores output by a neural network that was initially trained using data from patients that were treated by radiotherapy machines at other radiotherapy clinics. Such calibration techniques may enable the neural network to be trained using training data that is available while still providing accurate clinic-specific predictions.

Advantageously, by implementing the systems and methods described herein, a system may avoid the costs and processing resources that are typically required to generate large curated training data sets using data generated from data sources with a low amount of training data such as individual clinics. Moreover, the solution may allow for cross-clinical comparisons for models' performance in terms of reliability, may allow for comparing the confidence levels of different models, and may prevent overconfident predictions.

As will be described below, a central server (referred to herein as the analytics server) can train a neural network or other machine learning model using patient data from one or more radiotherapy clinics that utilize sets of radiotherapy machines. In a non-limiting example, the central server may transfer, or a processor of a local clinic may otherwise access, the trained neural network to a processor associated with the local clinic for calibration to the population at the clinic. Upon being calibrated, the neural network may predict treatment attributes that the clinicians and/or radiotherapy machines at the local clinic may use for patient treatment. FIG. 1 is a non-limiting example of components of a system in which the analytics server operates.

FIG. 1 illustrates components of a treatment attribute identification system 100. The system 100 may include an analytics server 110a, system database 110b, electronic data sources 120a-d (collectively electronic data sources 120), end-user devices 140a-e (collectively end-user devices 140), an administrator computing device 150, and radiotherapy clinics 160a-n (collectively radiotherapy clinics 160). The radiotherapy clinics 160 may be clinics at which patients may receive radiotherapy treatment, in some cases via one or more radiotherapy machines located within the clinic. The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110a may generate and display an electronic platform configured to use various computer models (including artificial intelligence and/or machine learning models) to identify and display treatment attributes (e.g., RTTP treatment attributes). The electronic platform may include graphical user interfaces (GUI) displayed on each electronic data source 120, the end-user devices 140, and/or the administrator computing device 150. An example of the electronic platform generated and hosted by the analytics server 110a may be a web-based application or a website configured to be displayed on different electronic devices, such as mobile devices, tablets, personal computer, and the like. In a non-limiting example, a physician operating the physician device 120b may access the platform, input patient attributes or characteristics and other data, and further instruct the analytics server 110a to generate an optimized RTTP. The analytics server 110a may utilize the methods and systems described herein to generate a treatment attribute and display the results on the end-user devices (e.g., the radiotherapy machine 140d) or adjust the configuration of one of end-user devices 140. The analytics server 110a may display the treatment attribute on the physician device 120b itself as well.

As described herein, treatment attributes may be or include any attributes related to treating patients at a radiotherapy clinic and/or using a radiotherapy machine. Treatment attributes may include, but are not limited to, different treatment modalities, field geometry settings for external beam radiotherapy, side effect predictions, organ and/or tumor segmentation, machine therapy attributes, dosage administration attributes (e.g., dosage amount), treatment frequency, treatment timing, etc. A system implementing the systems and methods described herein may provide calibrated predictions for one or more of any such treatment attributes for clinicians and/or radiotherapy machines to implement to treat patients.

The analytics server 110a may host a website accessible to users operating any of the electronic devices described herein (e.g., end users), where the content presented via the various webpages may be controlled based upon each particular user's role or viewing permissions. The analytics server 110a may be any computing device comprising a processor and non-transitory machine-readable storage capable of executing the various tasks and processes described herein. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each electronic data source 120 and/or end-user devices 140. Different users may use the website to view and/or interact with the predicted results.

The analytics server 110a may be configured to require user authentication based upon a set of user authorization credentials (e.g., username, password, biometrics, cryptographic certificate, and the like). The analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may also store data associated with each user operating one or more electronic data sources 120 and/or end-user devices 140. The analytics server 110a may use the data to weigh interactions while training various AI models accordingly. For instance, the analytics server 110a may indicate that a user is a medical professional whose inputs may be monitored and used to train the machine learning or other computer models described herein.

The analytics server 110a may generate and host webpages based upon a particular user's role within the system 100. In such implementations, the user's role may be defined by data fields and input fields in user records stored in the system database 110b. The analytics server 110a may authenticate the user and may identify the user's role by executing an access directory protocol (e.g. LDAP). The analytics server 110a may generate webpage content that is customized according to the user's role defined by the user record in the system database 110b.

The analytics server 110a may receive RTTP data (e.g., patient and treatment data) from a user or retrieve such data from a data repository, analyze the data, and display the results on the electronic platform. For instance, in a non-limiting example, the analytics server 110a may query and retrieve medical images from the database 120d and combine the medical images with RTTP data received from a physician operating the physician device 120b. The analytics server 110a may then use various models (stored within the system database 110b) to analyze the retrieved data. The analytics server 110a then displays the results (e.g., RTTP including couch and gantry angles) via the electronic platform on the administrator computing device, the electronic physician device 120b, and/or the end-user devices 140.

The electronic data sources 120 may represent various electronic data sources that contain, retrieve, and/or input data associated with RTTP (e.g., patient data and treatment data). For instance, the analytics server 110a may use the clinic computer 120a, physician device 120b, server 120c (associated with a physician and/or clinic), and database 120*d* (associated with the physician and/or the clinic) to retrieve/receive RTTP data associated with a particular patient's treatment plan.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110*a*. Specifically, the end-user devices 140 may include clinic computer 140*a*, clinic database 140*b*, clinic server 140*c*, a medical device, such as a CT scan machine, radiotherapy machine (e.g., a linear accelerator or a cobalt machine), and the like (140*d*), and a clinic device 140*e*.

The administrator computing device 150 may represent a computing device operated by a system administrator. The administrator computing device 150 may be configured to display data retrieved, treatment attributes generated by the analytics server 110*a* (e.g., various analytic metrics and/or field geometry) where the system administrator can monitor various models utilized by the analytics server 110*a*, electronic data sources 120, and/or end-user devices 140; review feedback; and/or facilitate training or calibration of the neural networks that are maintained by the analytic server 110*a*.

In operation, a physician may access an application executing on the physician device 120*b* and input RTTP data (e.g., patient information, patient diagnosis, radiation therapy treatment attributes, etc.). The analytics server 110*a* may then use a patient identifier to query patient data (e.g., patient anatomy and/or medical images) from the electronic data sources 120. The analytics server may then identify a clinic associated with the patient (e.g., clinic performing the treatment) and retrieve the neural network that is associated with the clinic (e.g., the neural network that has been calibrated based on a representative set of patient data of the clinic) based on a clinic identifier (e.g., an alphanumerical or numerical identifier that is associated with the clinic). The analytics server 110*a* may then utilize the systems and methods described herein to generate an optimized/uniform RTTP and display the results onto the physician device 120*b*, clinic computer 140*a*, and/or the medical device 140*d* (e.g., a display screen of the radiotherapy machine).

The analytics server 110*a* may be in communication (real-time or near real-time) with the medical device 140*d*, such that a server/computer hosting the medical device 140*d* can adjust the medical device 140*d* based on the treatment attributes generated by the analytics server 110*a*. For instance, the radiotherapy machine may adjust the gantry and couch based on angles and other attributes determined by the analytics server 110*a*. The analytics server 110*a* may transmit instructions to the radiotherapy machines indicating any number or type of treatment attributes (e.g., field geometry settings) to facilitate such adjustments.

The analytics server 110*a* may store machine learning models (e.g., neural networks, random forest, support vector machines, etc.), that are trained to predict treatment attributes to treat patients at radiotherapy clinics. The analytics server 110*a* may train the machine learning models using patient data of patients that are treated at radiotherapy machines 170*a*-*n* of the radiotherapy clinics 160. For instance, the analytics server 110*a* may receive patient data from processors of the radiotherapy clinics 160 and generate one or more sets of labeled training data indicating treatment attributes that were used to treat the patients at the respective radiotherapy clinics 160. The analytics server 110*a* may input the set of labeled training data into the stored machine learning models for supervised training to teach the machine learning models to predict confidence scores for treatment attributes for patient treatment. The analytics server 110*a* may continue to feed the training data into the machine learning models until the machine learning models are accurate to a threshold and store the models in a database of the analytics server 110*a*.

The machine learning models stored in the analytics server 110*a* may correspond to individual radiotherapy clinics or otherwise different sets of radiotherapy machines (e.g., radiotherapy machines that are located at individual radiotherapy clinics, are located in different geographical regions, treat specific types of diseases (e.g., different type of cancers), treat specific genders, etc.). For example, each machine learning model may be associated with an identifier indicating the radiotherapy clinic or set of radiotherapy machines for which it is configured to predict confidence scores for treatment attributes. An operator at a radiotherapy clinic may access an end-user device 140 located at the clinic or access an account associated with the clinic. The operator may provide an input at a user interface that causes the end-user device 140 to transmit a request to access a machine learning model that is associated with the clinic and/or the radiotherapy machines located within the clinic. The request may include an identifier associated with the machine learning model, the clinic, and/or the set of radiotherapy machines that the analytics server 110*a* may use as a key in a look-up table to identify the machine learning model. The analytics server 110*a* may receive the request and, in some cases, after authenticating the user, identify the machine learning model from the identifier. The analytics server 110*a* may transmit the identified machine learning model to the end-user device 140 or send an alert indicating the end-user device is authorized to access the model.

Upon receipt or access to the machine learning model, the end-user device 140 may perform the systems and methods described herein to calibrate the machine learning model to predict confidence scores and/or treatment attributes for the population of patients that is generally treated at the radiotherapy clinic and/or the respective set of radiotherapy machines. For example, the end-user device 140 may generate a calibration data set that includes data that represents the characteristics of patients that are generally treated at the clinic or by the set of radiotherapy machines. The end-user device 140 may input the calibration data set into the machine learning model to obtain confidence score outputs for a set of treatment attributes. For each patient, the end-user device 140 may identify the treatment attribute that is associated with the highest confidence score and generate a predicted treatment attribute data set from the identified treatment attributes. The end-user device 140 may input the predicted treatment attribute data set along with labels indicating the ground truth (e.g., the correct prediction for each of the predicted treatment attributes) into a calibration module (e.g., a set of executable instructions) including a calibration model (e.g., a machine learning model or an optimization model) that may be executed by the end-user device 140. Based on the input, the calibration model may output one or more calibration parameters that the end-user device 140 may use to calibrate any confidence score predictions that the machine learning model makes when predicting treatment attributes.

Upon determining the calibration parameters, the end-user device 140 may feed patient data for new patients into the machine learning model and use the calibration parameters to calibrate the output confidence scores for different treatment attributes. For example, the end-user device 140 may input each of the confidence scores and the calibration parameters into a function such as:

$$q_{hat}(x) = 1/\left(1 - e^{-\frac{z(x)}{T}}\right)$$

or $$q_{hat}(x) = sigm\left(\frac{z(x)}{T}\right)$$

where x is the predicted class (e.g., field geometry setting or other treatment attribute), $q_{hat}(x)$ is the calibrated confidence score, z(x) is a logit where $$z(x) = \log\left(\frac{p_{hat}(x)}{1 - p_{hat}(x)}\right)$$

where $p_{hat}(x)$ is the uncalibrated first confidence score, and T is the calibration parameter determined by the calibration model. The end-user device 140 may obtain a calibrated confidence score for each of the inputs and output the confidence scores and/or the corresponding treatment attributes to a user on a user interface of the end-user device 140. A user (e.g., a patient, doctor, clinician, etc.) may view the confidence scores and determine which treatment attributes to use for treatment.

Because the confidence scores have been calibrated (e.g., dampened or increased) based on the calibration parameters, the end-user device 140 may avoid displaying overconfident or inaccurate confidence scores that often occur in poorly trained machine learning models or models trained using a non-representative dataset. For example, a model without calibration may predict a class correctly, but may predict too strong of a confidence (e.g., 98%) when the confidence should have been much lower. By calibrating the neural network, the confidence scores may be adjusted to make the confidence score predictions more accurate.

Additionally or alternatively, instead of receiving the machine learning model, the end-user device 140 may access the machine learning model by transmitting instructions to the analytics server 110a to calibrate and/or use the machine learning model as described herein. The end-user device 140 may transmit patient data of patients treated at the respective radiotherapy clinic and/or the set of radiotherapy machines along with one or more flags or settings to the analytics server 110a to cause the analytics server 110a to generate calibration parameters. The analytics server 110a may generate a representative calibration data set from the patient data and generate one or more calibration parameters based on the flags or settings received from the end-user device 140 using the systems and methods described herein. After calibration, the analytics server 110a may input patient characteristics into the machine learning model and generate a set of calibrated confidence scores. The analytics server 110a may transmit the calibrated confidence scores and the corresponding treatment attributes back to the end-user device 140 for display.

Figure 2:
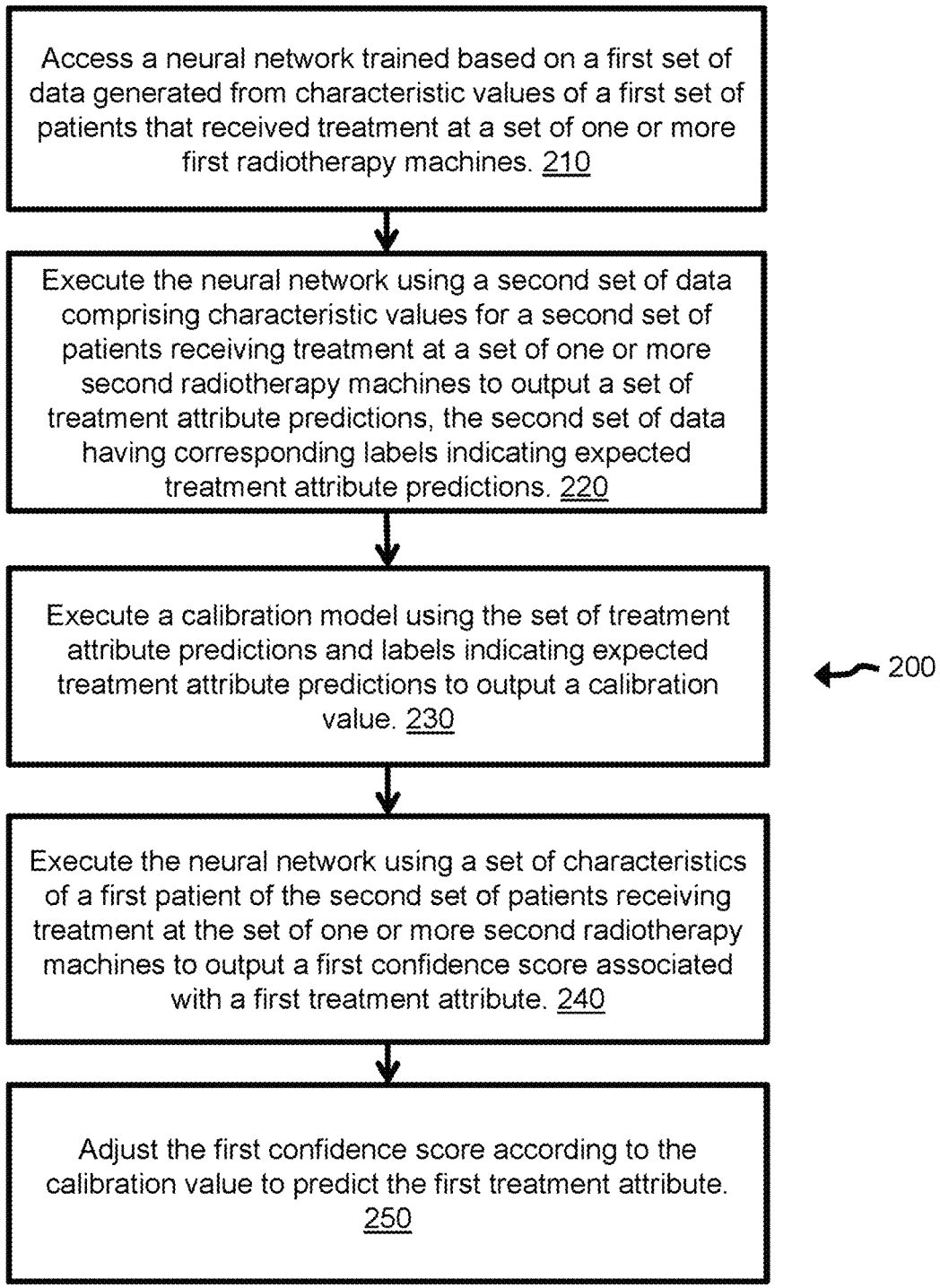
FIG. 2 illustrates a flow diagram of a process executed in a treatment attribute identification system, according to an embodiment.

FIG. 2 illustrates a flow diagram of a process executed in a treatment attribute identification system, according to an embodiment. The method 200 includes steps 210-250. However, other embodiments may include additional or alternative steps, or may omit one or more steps altogether. The method 200 is described as being executed by a data processing system (e.g., a computer similar to the data source 120, end-user device 140, or the analytics server 110a described in FIG. 1). However, one or more steps of method 200 may be executed by any number of computing devices operating in the distributed computing system described in FIG. 1. For instance, one or more computing devices may locally perform part or all of the steps described in FIG. 2 or a cloud device may perform such steps.

At step 210, a data processing system (e.g., the analytics server 110a or the end-user device 140) may access a neural network (or any other machine learning model such as random forest or a support vector machine) trained based on a first set of data generated from characteristic values of a first set of patients that received treatment at a set of one or more first radiotherapy machines. The neural network may be trained by the data processing system or by an external data processing system such as an external computer or server (e.g., the analytics server 110a). The set of one or more first radiotherapy machines may be radiotherapy machines that are located across radiotherapy clinics, that are located in different geographical regions (e.g., different cities, counties, states, etc.), that treat patients with different characteristics (e.g., that have different genders, weights, heights, body shapes, etc.), and/or that treat patients that have different diseases (e.g., patients with different types of cancers). Consequently, the set of patients may include patients with a diverse set of characteristics that can be used to train the neural network to predict treatment attributes for a wide range of people. The systems and methods described herein may be used to predict any treatment attributes for patients.

The neural network may be trained using supervised, semi-supervised, and/or unsupervised training or with a reinforcement learning approach. For example, the neural network may be trained to predict field geometry settings for a radiotherapy machine to use to treat patients. To do so, characteristic values of individual patients of the first set of patients may be input into the neural network with labels indicating the correct predictions for the patients. The neural network may output field geometry settings for individual patients based on their respective characteristics and the outputs can be compared against the labels. Using back-propagation techniques, the neural network may update its weights and/or parameters based on differences between the expected output (e.g., the ground truth) and the actual outputs to better predict future unseen cases (e.g., field geometry settings for future patients). Similar techniques may be used to train neural networks to predict any treatment attributes. A computer (e.g., the analytics server 110a) may continue this process until the neural network is sufficiently trained (e.g., accurate above a predetermined threshold). The computer may store the neural network in memory, in some cases upon determining the neural network has been sufficiently trained.

The data processing system may access the neural network via the cloud or by retrieving or receiving the neural network. For example, the data processing system may transmit a password or token to a device storing the neural network in the cloud to access the neural network. In another example, the data processing system may receive or retrieve the neural network either automatically responsive to the neural network being sufficiently trained or responsive to a GET request from the data processing system. The data processing system may transmit a request for the neural network responsive to a request at a user interface of the data processing system by a user. Upon receiving the neural network, the data processing system may store the neural network in memory for retrieval when the data processing system makes predictions for treatment attributes for individual patients that receive treatment at the set of radiotherapy machines with which the neural network is associated.

At step 220, the data processing system may execute the neural network using a second set of data comprising characteristic values of a second set of patients receiving treatment at a set of one or more second radiotherapy machines to output a set of treatment attribute predictions, the second set of data may have corresponding labels indicating expected treatment attribute predictions. The second set of radiotherapy machines may be located at a specific radiotherapy clinic, located within a specific geographical area, treat specific populations of patients (e.g., specific genders, weights, heights, etc.), treat specific types of disease (e.g., tumors located in specific areas), or be related in any other way. The data processing system may be configured to receive patient attributes for a patient being treated at a radiotherapy machine of the second set of radiotherapy machines and input the patient attributes into the neural network to obtain treatment attributes such as field geometry settings for treatment. The neural network may not be trained, or may only be partially trained, based on patient data of patients that received treatment at the second set of radiotherapy machines (e.g., in instances in which such data is not available or too expensive to generate during the training phase of the neural network). Thus, there may be a need to calibrate the neural network to provide accurate predictions for patients being treated at the second set of radiotherapy machines.

The second set of data may be or include a calibration data set that is representative of the population of people that are treated at the set of one or more second radiotherapy machines. For example, if the set of one or more second radiotherapy machines generally treats a high ratio of females to males, the calibration data set may include characteristics of patients with the same or a similar ratio (e.g., within a threshold). In another example, if the set of one or more second radiotherapy machines generally only treats patients that have breast and lung cancer, the calibration data set may only include characteristics of patients with breast and lung cancer. The calibration data set may further include a similar ratio of patients with breast cancer to patients with lung cancer. Calibration data sets may similarly include data of patients that is representative of multiple characteristics of the population of patients that were treated at the set of second radiotherapy machines. The calibration data set may be representative of populations of patients having any number of characteristics.

The data processing system may execute the neural network by sequentially feeding the second set of data into the neural network for individual patients. For each patient, the data processing system may generate a vector comprising values of the characteristics of the patient (e.g., height, weight, gender, tumor size, tumor location, age, prescribed dosage, body mass index, image data of targets and organs, etc.) and input the vector into the neural network. The neural network may receive the vector and output confidence scores for different treatment attribute predictions based on the weights and parameters the neural network acquired during training.

For example, the neural network may be trained to predict whether to use standard field geometry settings or customized field geometry settings to treat patients. Upon receiving an input of characteristics of a particular patient that is about to be treated at a radiotherapy machine of the one or more second radiotherapy machines, the neural network may predict confidence scores for both the potential outputs of standard field geometry settings and customized field geometry settings. The confidence scores may indicate the certainty that each potential output is the correct output. The following vector illustrates example prediction outputs (e.g., labels associated with the highest predicted confidence scores) for four different patients by such a neural network:

$(y_{hat}, p_{hat}) = <1, 0.96; 0, 0.98; 1, 0.86; 0, 0.9>$ where $y_{hat}$ is the predicted field geometry setting label where 1 is standard field geometry setting and 0 is a customized field geometry setting and $p_{hat}$ is the confidence score associated with the label.

In another example, the neural network (or a different neural network) may be trained to predict whether a particular treatment has harmful side effects. The neural network may have the potential outputs of "no harmful side effects (label=0)," "mild side effects (label=1)," and "serious side effects (label=2)." Upon receiving an input of characteristics of a patient (which may include a delivered dose distribution), the neural network may output confidence scores for each potential output indicating a likelihood that the patient will experience side effects of the associated class. The following vector illustrates example prediction outputs (e.g., labels associated with the highest predicted confidence scores) for four different patients by such a neural network:

$(y_{hat}, p_{hat}) = <1, 0.86; 2, 0.75; 1, 0.8; 1, 0.68>$ where $y_{hat}$ is the predicted side effect label according to the above labels and $p_{hat}$ is the confidence score associated with the label (e.g., the likelihood the patient will experience the respective side effect).

In addition to patient characteristics, the calibration data set may include labels indicating the correct treatment attribute predictions for individual patients (e.g., the ground truth of the calibration data set). For example, the calibration data set may include labels indicating the known correct treatment or known outcome for the characteristics that are input into the machine learning model. Such labels may be used to calibrate the neural network as will be described below. The following vector illustrates example ground truth labels for four different patients to input into two machine learning models (e.g., a machine learning model configured to predict field geometry setting labels and a machine learning model configured to predict side effect labels):

(field geometry setting label, side effect label)=<0,0; 0,2; 1, 1; 0,1>.

At step 230, the data processing system may execute a calibration model using the set of treatment attribute predictions and labels indicating expected treatment attribute predictions to output a calibration value. The calibration model may be another machine learning model (e.g., a neural network, support vector machine, random forest, etc.) that is trained to predict calibration parameters for machine learning models such as the neural network based on predicted outputs of the neural network and the corresponding labels that indicate the ground truth of such outputs. The calibration model may be an optimization model (e.g., a conjugate gradient solver) that can numerically or analytically determine the calibration parameters based on the same inputs.

For example, the data processing system may input a calibration data set into the neural network that includes characteristics for multiple patients. For each patient, the neural network may predict confidence scores for multiple treatment attributes. The data processing system may compare the confidence scores that are associated with the treatment attributes and identify the treatment attribute that is associated with the highest confidence score as the predicted treatment attribute. The data processing system may feed the identified treatment attributes along with the label or ground truth treatment attribute that corresponds to the respective patient into the calibration model to obtain a calibration value specific to the neural network that is being calibrated.

The calibration model may be configured to determine calibration parameters that minimize cross-entropy loss using models such as a neural network model or with the following equation:

$$H(p, q) = -\sum_x y(x)\log q(x)$$

where x indexes the different classes, y(x) is $y_{true}$ for class x, $$q(x) = 1 / \left(1 - e^{-\frac{z(x)}{T}}\right) \text{ where } z(x) = \log\left(\frac{p_{hat}(x)}{1 - p_{hat}(x)}\right),$$

and T is the calibration parameter. The following is an example input for two samples in a set with three classes (e.g., treatment attributes):

$z(x)$=[[4.0, 2.0, 1.0], [5.0, 6.0, 1.0]]

labels=$y_{true}$=[[1.0, 0.0, 0.0], [0.0, 1.0, 0.0]]

By implementing the equation or a neural network, the data processing system may find optimal calibration parameters to use to calibrate the neural network.

Before identifying the treatment attribute that is associated with the highest confidence score as the predicted treatment attribute, the data processing system may compare the confidence score to a threshold. The data processing system may determine the treatment attribute is associated with the correct prediction responsive to the confidence score exceeding the threshold. If the confidence score does not exceed the threshold, the data processing system may generate a null value to input into the calibration model with a corresponding null label to avoid calibrating the neural network based on a prediction for which the neural network has low confidence. Thus, the data processing system may calibrate the neural network only using predictions for which the neural network is confident, increasing the accuracy of the calibration and avoiding calibrating the model based on "guesses."

The calibration parameters may include a vector or set of parameters. Such parameters may include any number of parameters depending on the calibration algorithm that is used to calibrate the neural network. For example, in the case of temperature scaling, the parameters may only include one "temperature" value that can be used to calibrate the output confidence scores of the neural network. The temperature value may be used to dampen predictions from the neural network model, thus minimizing the number of overconfident predictions that are made by the neural network. Other calibrations methods may include histogram binning and isotonic regression. Any number of calibration parameters may be used to adjust the confidence scores that are output by the neural network.

In instances in which the calibration model is a neural network or another machine learning model, the neural network may be trained using any of a supervised, semi-supervised, or unsupervised training method. For example, the neural network may be trained using training data including predicted labels and ground truth labels. The neural network may be trained using such training data until the neural network is accurate above a threshold. Upon exceeding the accuracy threshold, the data processing system may use the calibration neural network to predict a temperature (or other set of parameters depending on the chosen calibration model) for the neural network that is configured to predict treatment attributes for patients being treated at the second set of radiotherapy machines.

At step 240, the data processing system may execute the neural network using a set of characteristics of a first patient of the second set of patients receiving treatment at the set of one or more second radiotherapy machines to output a first confidence score associated with a first treatment attribute. The data processing system may receive values of characteristics of the patient from a user (e.g., a clinician, doctor, or the patient themselves) via a user interface and generate a feature vector that includes the values. Additionally or instead, the data processing system may retrieve values of characteristics of the patient from storage to include in the feature vector responsive to receiving an identifier of the patient. The data processing system may input the feature vector into the neural network and obtain an output from the neural network including confidence scores for different treatment attributes (e.g., different field geometry settings).

The data processing system may receive the characteristics for the patient based on a patient identifier that is provided at a user interface. For example, a clinician may input the name of the first patient into the user interface at an end-user device and the end-user device may transmit the name to the data processing system. The data processing system may use the patient's name to query a database that includes patient information and retrieve information about the patient such as the patient's electronic health data records. For instance, the data processing system may query the database for data associated with the patient's anatomy, such as physical data (e.g., height, weight, and/or body mass index) and/or other health-related data (e.g., blood pressure or other data relevant to the patient receiving radiation therapy treatment) and/or geometrical data. The data processing system may also retrieve data associated with current and/or previous medical treatments received by the patient (e.g., data associated with the patient's previous surgeries).

If necessary, the data processing system may also analyze the patient's medical data records to identify the needed patient characteristics. For instance, the data processing system may query a database to identify the patient's body mass index (BMI). However, because many medical records are not digitalized, the data processing system may not receive the patient's BMI value using simple query techniques. As a result, the data processing system may retrieve the patient's electronic health data and may execute one or more analytical protocols (e.g., natural language processing) to identify the patient's body mass index. In another example, if the data processing system does not receive tumor data (e.g., end-points) the data processing system may execute various image recognition protocols and identify the tumor data.

The data processing system may receive additional data from one or medical professionals. For instance, a treating oncologist may access a platform generated/hosted by the data processing system and may add, remove, or revise data associated with a particular patient, such as patient attributes, treatment attributes, tumor attributes, primary site of treatment, tumor stage, end-point, whether the primary tumor has been extended, and the like. Because tumor staging and the end level attributes are sensitive information that affect patient treatment, this information is typically inputted by the treating oncologist.

The data received by the data processing system (e.g., patient/treatment data) may belong to three categories: numerical, categorical, and visual. Non-limiting examples of numerical values may include patient age, physical attributes, and other attributes that describe the patient. Non-limiting examples of categorical values may include different stages of treatment or disease associated with the patient. Visual data may include medical images representing the patient and his/her treatment regions, such as CT scans or other scans illustrating the patient's tumor.

Another example of a patient characteristic may include specific tumor locations. More specifically, this data may indicate the primary tumor location with respect to the patient's centerline. This data may be inputted by the treating oncologist or may be analyzed using various image recognition or segmentation methods executed on the patient's medical images. This information can also be predicted using the machine learning model if it is not inputted by the treating oncologist (or otherwise received by the data processing system). Another patient attribute may indicate whether and how close the tumor is to other non-diseased organs. For instance, a tumor to be eradicated may be millimeters away from another organ. This information may change field geometry, as other organs must be avoided.

Another example of a patient characteristic may include whether the patient uses a prosthesis (e.g., hip or femoral head prosthesis). This characteristic may result in a change in the patient's treatment (e.g., a change in confidence score for a particular treatment because patients with these conditions might require a special treatment).

The neural network may receive such characteristics about the first patient and output confidence scores for one or more treatment attributes. The first confidence score may be the highest confidence score of the confidence scores that were output by the neural network and may correspond to the data processing system's treatment prediction for the first patient (e.g., the first treatment attribute). The data processing system may identify the first confidence score responsive to comparing the predicted confidence scores and identifying the highest confidence score as the first confidence score. The data processing system may determine the first treatment attribute associated with the first confidence score is the correct prediction responsive to determining the first confidence score is the highest predicted confidence score. In some instances, the first treatment attribute may be a dosage amount or a field geometry setting such as an angle associated with a couch or a gantry of the radiotherapy machine, a set of standard field geometry settings, one or more customized field geometry settings, an arc length of the gantry, a number of arcs, a positioning of the couch or gantry, length of time to apply a prescribed dosage, etc. The first treatment attribute may be any treatment attribute as described herein.

For example, the neural network may be configured to output confidence scores for different arc length field geometry settings for a radiotherapy machine. Each confidence score may be associated with a different arc length. The data processing system may input the characteristics for the first patient into the neural network and the neural network may output confidence scores for each arc length setting. The data processing system may identify the arc length field geometry setting that is associated with the highest confidence score as the correct setting.

In another example, the neural network may predict confidence scores for field geometry settings that indicate the location to place the isocenter of the radiotherapy machine and/or an arc length or path for the gantry of the radiotherapy machine. As used herein, the isocenter (or the radiation isocenter) refers to the point in space where radiation beams intersect when the gantry rotates (e.g., half or full arcs) during the "beam-on" mode. For example, the neural network may predict a high confidence score for a field geometry setting that places the isocenter in the middle of the tumor and has a full arc gantry motion while the beam is on. Such may be the case when the patient has a high BMI or needs to avoid other machines that are treating the patient (e.g., a ventilator). In another example, the neural network may predict a high confidence score for a field geometry setting that has a few fixed tube directions that are evenly distributed and that attempts to avoid certain structures/organs of the patient's body.

In another example, the neural network may predict a field geometry setting for a patient to receive volumetric modulated arc therapy (VMAT) in one or more arcs. Different settings may be associated with different numbers of arcs. The neural network may make such predictions when the patient exceeds a certain height and/or weight. In another example, the neural network may predict a high confidence score for a field geometry setting of two partial arcs when a patient is connected to a ventilator. Technicians that operate radiotherapy machines at different radiotherapy clinics that treat different types of patients may treat similar patients using different numbers of arcs and/or treatments based on the experiences of the physicians and/or the treatments that are effective in the area, emphasizing the need for the neural network to be calibrated to patients being treated by the radiotherapy machine and/or radiotherapy clinic.

The data processing system may determine a probability that an event will occur based on the output confidence score. For example, the neural network may be configured to output confidence scores that a given treatment will produce serious side effects. The neural network may include an output node associated with a serious side effect prediction. The data processing system may input the characteristics for the first patient into the neural network and the neural network may output a confidence score for the serious side effect prediction. The confidence score may indicate a percent risk of the first patient experiencing serious side effects for the treatment.

At step 250, the data processing system may adjust the first confidence score according to the calibration value to predict the first treatment attribute. The data processing system may adjust the first confidence score in addition to or instead of any other confidence scores that the neural network predicted for the first patient. To adjust the first confidence score, the data processing system may input the first confidence score into a calibration module that comprises instructions to receive confidence scores and the determined calibration parameters and adjust the confidence scores according to the determined calibration parameters for calibration.

For example, using the calibration module, the data processing system may adjust the first confidence score using one of the following equations:

$$q_{hat}(x) = 1 / \left(1 - e^{-\frac{z(x)}{T}}\right)$$

or $$q_{hat}(x) = sigm\left(\frac{z(x)}{T}\right)$$

where x is the predicted class (e.g., treatment attribute), $q_{hat}(x)$ is the calibrated confidence score, $z(x)$ is a logit where $$z(x) = \log\left(\frac{p_{hat}(x)}{1 - p_{hat}(x)}\right)$$

where $p_{hat}(x)$ is the uncalibrated first confidence score, and T is the calibration parameter determined by the calibration model. The data processing may input the first confidence score (and any other confidence scores that were output by the neural network) into the calibration module and obtain a calibrated confidence score in return. Note that the calibration module may be or include any equation or equations that use calibration parameters to calibrate prediction scores for treatment attributes.

Responsive to obtaining the calibrated confidence scores, the data processing system may render the scores along with the corresponding treatment attributes on a user interface. A user, clinician, or doctor may view the results and decide the best course of treatment accordingly (e.g., implement the treatment that is associated with the highest confidence score or select a treatment from a group of treatments associated with the highest confidence scores). Advantageously, because the data processing system may determine and render confidence scores that are calibrated to provide treatment recommendations to populations of patients that are treated at the radiotherapy machine of a set of radiotherapy machines that treat a common subset of people, patients and doctors can view the predicted confidence scores and be confident in the scores' accuracy. Thus the patients and doctors may determine the best course of action using accurate data. Systems that do not utilize such calibration techniques may offer overconfident predictions that doctors and patients may not trust, causing the patients or doctors to ignore the predictions to instead determine a new course of action.

The data processing system may only display confidence scores that satisfy a predetermined criteria. For example, the data processing system may only display the highest calibrated confidence score or a predetermined number of the highest confidence scores to a user. The data processing system may identify the highest calibrated confidence scores (e.g., the calibrated first confidence score) and only display the highest calibrated confidence scores on a user interface of a display. In another example, the data processing system may only display the highest calibrated confidence score responsive to determining the confidence score exceeds a threshold (e.g., a predetermined threshold set by a user). By using such criteria, the data processing system can control the confidence scores and the corresponding treatment attributes that are displayed to users, thus ensuring users only view confidence scores for treatment attributes for which the neural network made confident predictions and do not get distracted by other predictions.

However, responsive to determining none the output confidence scores by the neural network satisfy the criteria (e.g., the highest confidence score of a set of predicted outputs is lower than a threshold), the data processing system may generate an alert indicating a treatment attribute could not be predicted. The data processing system may transmit the alert to be displayed on a user interface of the radiotherapy machine, a clinic computer, and/or end-user computer. The alert may include text indicating the criteria was not satisfied, the predicted confidence scores (e.g., all or a predetermined number of the highest confidence scores), and/or the corresponding treatment attributes. The alert may be displayed on the respective device and a user may view the treatment attributes and corresponding confidence scores to make a treatment decision.

The data processing system may use the same calibration value to calibrate the predictions for the neural network for any number of patients without any further training or adjustment of the calibration value. For example, the data processing system may execute the neural network using a set of characteristics of a second patient receiving treatment at the set of one or more second radiotherapy machines. The neural network may output a confidence score associated with a treatment attribute (e.g., the first treatment attribute or a different treatment attribute that is associated with a highest confidence score). The neural network may adjust the confidence score for the new treatment attribute according to the same calibration parameter that was used to calibrate the confidence score for the first patient. The data processing system may compare the calibrated confidence score to other calibrated predicted confidence scores and/or to a set of criteria (e.g., a threshold). Responsive to determining the criteria is satisfied and/or that the confidence score is the highest of the predicted confidence scores, the data processing system may output the calibrated confidence score and/or the second treatment attribute to a user interface indicating the second treatment attribute as the predicted treatment attribute.

In addition to or instead of displaying the calibrated confidence scores for the potential treatment attributes to treat a patient, the data processing system may transmit instructions to a radiotherapy machine of the second set of radiotherapy machines to adjust the machine's configuration. For example, the data processing system may automatically transmit instructions to cause the radiotherapy machine to treat a patient for which the neural network predicted a field geometry setting (e.g., a field geometry setting associated with a highest confidence score and/or a confidence score that exceeds a threshold). The instructions may include a flag or setting that causes the radiotherapy machine to treat the patient using the predicted field geometry setting. Upon receipt of the instructions and, in some cases, receipt of an indication (e.g., an input on a user interface) indicating the patient is positioned to be treated, the radiotherapy machine may automatically treat the patient using the predicted field geometry setting. Advantageously, because the confidence scores for the treatment attributes are calibrated before they are compared to the threshold, the system can ensure that any automatic adjustments to the field geometry settings of the radiotherapy machine, or any other radiotherapy machine attribute, may be accurate and not based on an inaccurate or overconfident prediction.

Additionally or alternatively, instead of automatically treating the patient with the predicted treatment attribute, the radiotherapy machine may treat the patient with the predicted treatment attribute responsive to receiving an input at a user interface (e.g., a user interface displayed at clinic computer or an end-user computer). For example, the data processing system may transmit an indication of the predicted treatment attribute (e.g., predicted field geometry setting) and the associated confidence score of the treatment attribute to the radiotherapy machine or a clinic computer or end-user computer. The confidence score and the treatment attribute may be displayed on a display of the radiotherapy machine or the clinic computer or end-user computer. A user (e.g., the patient, a clinician, a doctor, etc.) may view and select the confidence score and/or treatment attribute. Responsive to receiving the selection, the radiotherapy machine may adjust its configuration to treat the patient according to the selected treatment attribute.

For example, the data processing system may determine confidence scores for field geometry settings for different VMAT arcs. For instance, for a particular patient's treatment, the data processing system may use the systems and methods described herein to determine calibrated confidence scores for four unique VMAT arcs (e.g., accelerator arcs that can be used for treatment). For each arc, the data processing system may further determine (e.g., with one or more other calibrated or uncalibrated machine learning models or the same machine learning model that determined the confidence scores for the respective arc) and display confidence scores for characteristics of the arcs such as collimator angle, couch angle, gantry endpoint, gantry starting point, isocenter location attributes (in each axis), VMAT type, X1 and X2 jaw values, etc. An end-user (e.g., technician and/or treating oncologist or any other medical professional viewing the graphical user interface) may add, revise, and/or overwrite any of the depicted values and provide an input that causes the respective radiotherapy machine to treat the patient using the selected VMAT arc and the arc characteristics.

Additionally or alternatively, the data processing may transmit multiple calibrated confidence scores and treatment attributes (e.g., a predetermined number of the highest confidence scores of the predicted scores and/or scores that exceed a threshold) to the radiotherapy machine, the clinic computer, or the end-user computer. In such instances, the confidence scores and associated treatment attributes may each be displayed so a user may select the attribute to use to configure the radiotherapy machine or to otherwise treat the patient.

When the user performs an activity on the electronic platform, the data processing system may track and record details of a user's activity. For instance, when a predicted result is displayed on a user's electronic device, the data processing system may monitor the user's electronic device to identify whether the user has interacted with the predicted results by editing, deleting, accepting, or revising the results. The data processing system may also identify a timestamp of each interaction, such that the data processing system records the frequency of modification, duration of revision/correction.

The data processing system may utilize an application programming interface (API) to monitor the user's activities. The data processing system may use an executable file to monitor the user's electronic device. The data processing system may also monitor the electronic platform displayed on an electronic device via a browser extension executing on the electronic device. The data processing system may monitor multiple electronic devices and various applications executing on the electronic devices. The data processing system may communicate with various electronic devices and monitor the communications between the electronic devices and the various servers executing applications on the electronic devices.

The neural network may be trained using a supervised method using patient data of patients that were treated at one or more of the second set of radiotherapy machines. For instance, during operation, the neural network may predict confidence scores for field geometry settings. The data processing system may calibrate the confidence scores, identify the highest confidence score or that otherwise satisfies a threshold, and display the calibrated confidence score and/or the corresponding field geometry setting on a user interface. Users may either select the predicted field geometry settings via the user interface to configure the respective radiotherapy machine according to the predicted field geometry setting or provide an input to indicate the predicted field geometry setting was not used to treat the respective patient. The device that received the user input may transmit a signal back to the data processing system indicating the user input along with the predicted field geometry setting and/or a patient identifier of the patient that was treated. The data processing system may receive the signal, identify the data that was used to make the prediction (e.g., via the patient identifier), and label the data according to the user input (e.g., a 1 to indicate the prediction was used to adjust the configuration of the radiotherapy machine and a 0 to indicate the prediction was not used). The data processing system may feed the labeled data into the neural network for training. Similar methods of supervised may be used to train models that predict any type of treatment attribute based on an input that indicates whether the predicted treatment attribute was implemented.

Responsive to training the neural network with data sets of one or more patients, the data processing system may recalibrate the neural network by determining one or more new calibration parameters for the newly trained neural network. The data processing system may determine new calibration parameters because the previous calibration parameters were determined based on how the neural network was previously weighted and may not be accurate for the new weights or parameters that result from the further training. The data processing system may determine the calibration parameters for the neural network in the same manner as described above. When calibrating the neural network, the data processing system may use the same calibration data set or a different calibration data set that is similarly representative of the population of patients that are treated at the set of one or more second radiotherapy machines. The data processing system may determine the new calibration parameters and make treatment attribute predictions for future patient treatments using the new calibration parameters until the neural network is further trained and/or recalibrated.

Additionally or alternatively, the data processing system may utilize multiple neural networks or machine learning models to obtain a prediction for a treatment attribute for a patient. Each of the neural networks may have been trained by patient data of patients that were treated outside of the second set of radiotherapy machines and may be accessed by the data processing system as described above. The data processing system may use the same or different calibration data sets for each neural network to determine calibration values for each neural network. For example, the data processing system may use the same calibration data set to calibrate multiple neural networks that are associated with treating patients at a radiotherapy clinic. However, because the neural networks may have been initially trained based on a different sets of training data, the calibrations parameter(s) for each of the neural networks may be different. Upon being calibrated, the data processing system may input the same patient characteristics of a patient to each of the neural networks to obtain confidence scores for one or more treatment attributes to use to treat the patient.

In one example, the data processing system may compare the output confidence scores from each of the neural networks with each other. The data processing system may identify the highest confidence score and select the treatment attribute that is associated with the highest confidence score for display and/or to automatically use to treat the patient with the radiotherapy machine. Advantageously, by using multiple neural networks, the data processing system may identify the treatment attribute for which a neural network is the most confident as the correct treatment attribute prediction and present a recommendation to use the treatment attribute for treatment. Using multiple neural networks may provide the data processing system with more data to select treatment attributes, enabling more informed decisions. Further, because each of the neural networks is individually calibrated, the highest calibrated confidence score may be more likely to be accurate and/or be associated with the correct treatment attribute than predictions that are made based on multiple uncalibrated models or a calibrated model.

In another example, the data processing system may aggregate the corresponding output confidence scores (e.g., confidence scores for identical treatment attributes) of each of the neural networks to determine the treatment attribute to predict. The data processing system may aggregate the confidence score outputs across neural networks and compare the aggregated confidence scores of each treatment attribute with each other. The data processing system may select the treatment attribute that is associated with the highest confidence score as the predicted treatment attribute for display or to adjust the radiotherapy machine for treatment. Thus, the data processing system may crowdsource confidence score predictions from multiple calibrated neural networks to identify treatment attribute predictions, further improving the accuracy of such predictions and avoiding the use of a single inaccurate and/or overconfident confidence score prediction.

Using the systems and methods described herein, the data processing system can have a formalized approach to generate a treatment attribute in a single automated framework based on various variables, parameters, and settings that depend on the patient, the patient's treatment, and/or the clinic. The systems and methods described herein enable a central server or a processor associated with (e.g., located in) a local clinic to generate treatment attributes that are optimized for individual patients based on the standard treatments at the clinic, replacing the need to depend on a technician or doctor's subjective skills and understanding. The systems and methods may enable the central server or processor to do so without using training data from patients being treated at the clinic, which may not always be available.

Figure 3:
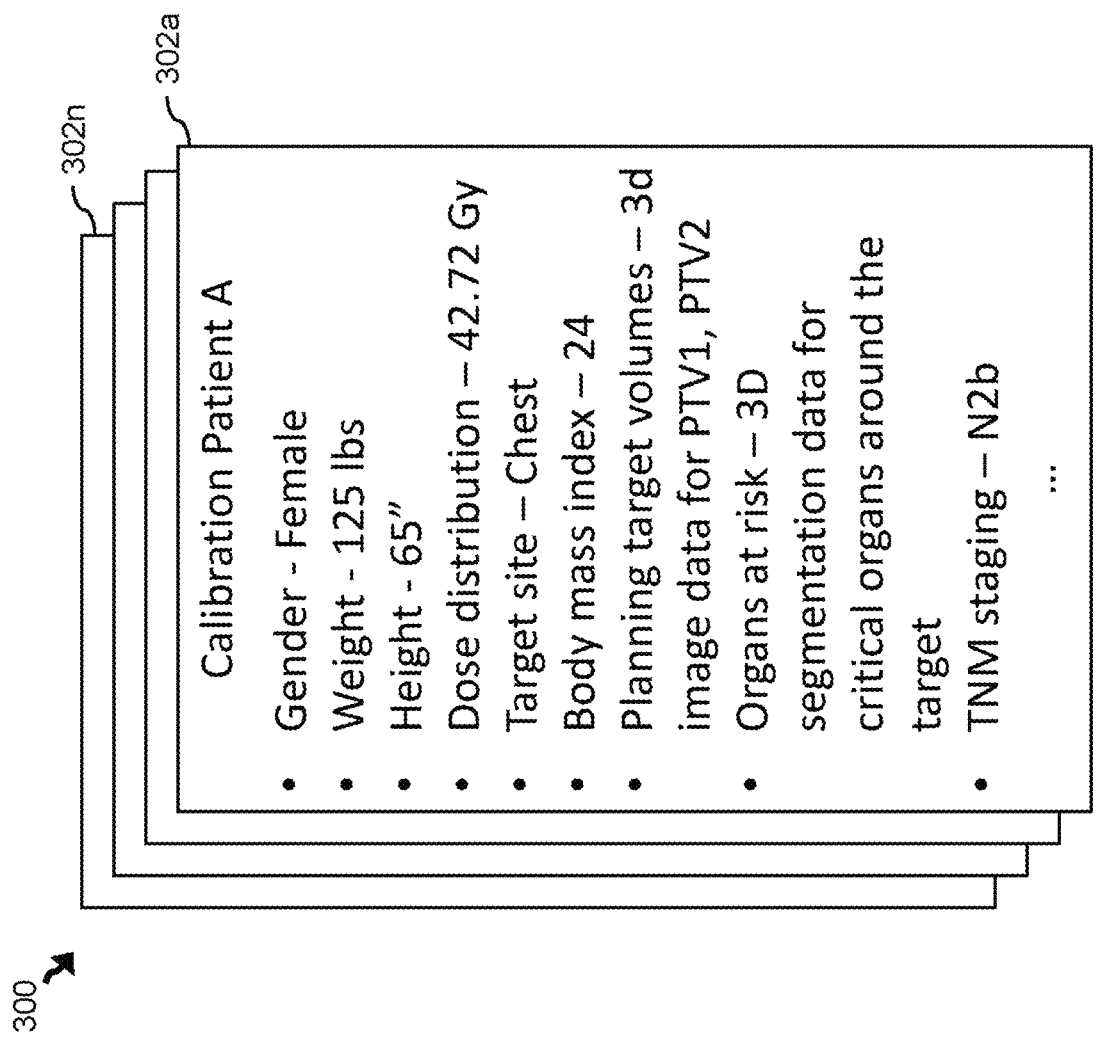
FIG. 3 illustrates an example calibration data set, according to an embodiment.

Referring now to FIG. 3, a non-limiting example of a calibration data set 300 is illustrated. The calibration data set 300 may include a plurality of calibration patient data sets 302a-n (hereinafter described as calibration patient data sets 302 or calibration patient data set 302). The calibration patient data sets 302 may be fed into a machine learning model (e.g., an externally trained machine learning model) such as a neural network, as described above, to generate field geometry predictions, or other predictions relating to RTTP treatment. The calibration data set 300 may include any number of calibration patient data sets 302. The calibration data set 300 may be considered one or multiple data sets.

Each calibration patient data set 302 may include one or more patient characteristics or attributes indicating characteristics of a particular patient. The characteristics or attributes may include values identifying characteristics of the patient, how the patient is currently being treated (e.g., radiation dose distribution and/or other aspects of RTTP), TNM staging information, and/or the location on which the patient is experiencing a problem that may be treated through radiotherapy (e.g., the location, size, and/or shape of a tumor). The characteristics or attributes may additionally or instead include image data of targets or organs of the patient. In a non-limiting example, a patient data set may include data relating to the gender, weight, height, dose distribution, target organ, body mass index, geometry, etc., of a patient. The calibration patient data sets 302 may include any attributes or characteristics of patients.

The calibration data set 300 may be representative of the patient population that is treated at a particular radiotherapy clinic or by radiotherapy machines that are located within a geographical region. For example, different radiotherapy machines and/or radiotherapy clinics may treat people with different types of problems and/or use different methods to treat such problems. Examples may include different machines or clinics may treat different gender ratios, people with different types of problems, different weight distributions, people that are susceptible to different types and extremes of side effects, etc. Such representative data sets may be manually selected or selected by a computer by identifying an average baseline for different characteristics of patients and identifying patients that have characteristics that, upon being aggregated together, match or are within a threshold of the average baseline. Advantageously, because the calibration data set 300 may be representative of the population that is treated at a clinic or a particular set of machines, the data set may be used to accurately calibrate a machine learning model to predict treatment attributes to treat patients at the clinic or set of radiotherapy machines. Systems that do not use such a representative calibration data set may cause the machine learning model to be inaccurately calibrated, reducing the accuracy of confidence score predictions by the machine learning model.

Figure 4:
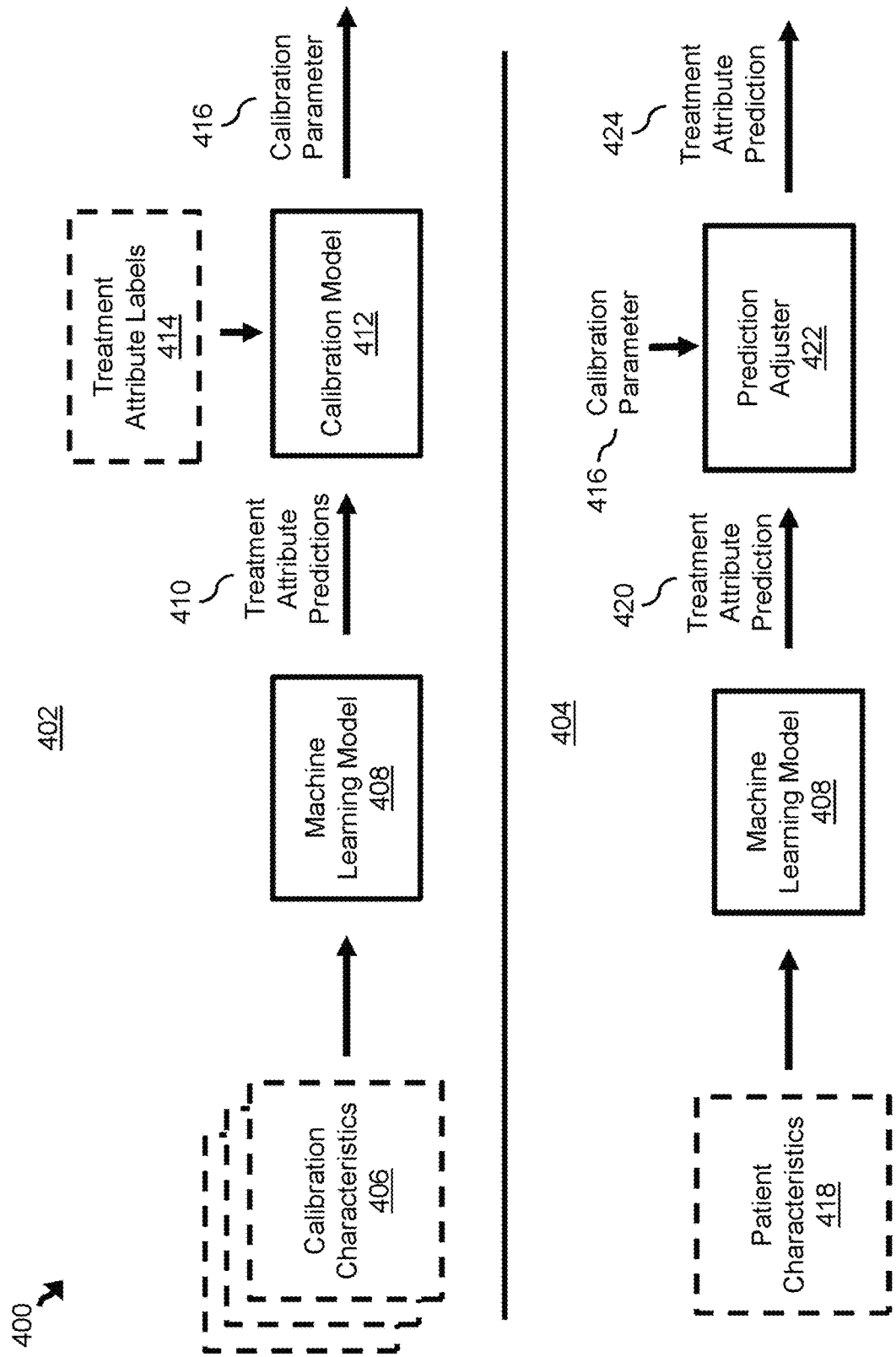
FIG. 4 illustrates an example flow diagram of a process executed in a treatment attribute identification system, according to an embodiment.

Referring now to FIG. 4, a non-limiting example of sequences 400 for calibrating a machine learning model and using the machine learning model to predict field geometry predictions to treat a patient is illustrated. The sequences 400 may include a sequence 402 for generating a calibration parameter for a machine learning model and a sequence 404 for using the calibration parameter to make field geometry setting (or other treatment attribute) predictions for a patient.

In the sequence 402, the calibration characteristics 406 may be input into a machine learning model 408. The calibration characteristics 406 may be representative of a population of patients that are treated by a set of radiotherapy machines at one or more radiotherapy clinics. For instance, in a non-limiting example, the calibration characteristics 406 may represent people that are treated at radiotherapy machines in the northwest region of the United States or at a local clinic within the same region. Calibration characteristics 406 for individual patients may be sequentially input or inserted into the machine learning model 408 by a computer, such as a computer at a clinic, or in the cloud. The machine learning model 408 may output an RTTP prediction such as treatment attribute predictions 410 indicating predicted treatment for each of the patients.

The machine learning model 408 may be any machine learning model such as a neural network, random forest, support vector machine, etc. The machine learning model 408 may have been trained to predict different treatment attributes such as treatment modalities, field geometry settings, symptom likelihoods, etc. The machine learning model 408 may have been trained using data from patients that were treated at radiotherapy machines outside of the set of radiotherapy machines described above. A computer at a radiotherapy clinic (e.g., that is associated with the set of radiotherapy machines) may access the machine learning model 408 by retrieving or receiving the machine learning model 408 (e.g., via an HTTP GET request) or by accessing a cloud database or server in which the machine learning model 408 is stored. Upon accessing the machine learning model 408, the computer may input the calibration characteristics 406 into the machine learning model 408 to obtain treatment attribute predictions 410.

Upon generating the treatment attribute predictions 410 for each of the patients of the calibration characteristics 406, the computer may input the treatment attribute predictions 410 into a calibration model 412 along with treatment attribute labels 414 representing the ground truth associated with the treatment attribute predictions 410 (e.g., the correct labels that correspond to the calibration characteristics). For instance, the treatment attribute predictions 410 may be a vector including binary values indicating whether patients should be treated with standard field geometry settings. The treatment attribute labels 414 may be a vector of the same size indicating the correct prediction (e.g., the correct binary value) for each patient. The calibration model 412 may be a machine learning model, such as a neural network, or an optimization algorithm that is configured to receive the treatment attribute predictions 410 and treatment attribute labels 414 and output one or more calibration parameters 416 based on the treatment attribute predictions 410 and treatment attribute labels 414.

The calibration parameter 416 may be one or more calibration parameters that may be used to calibrate confidence scores for different labels or classifications that are output by the machine learning model 408. For instance, the calibration parameter 416 may be a temperature value that may be used in temperature scaling to adjust confidence scores that are output by the machine learning model 408. The calibration parameter 416 may be any calibration value output by the calibration model 412. The calibration parameter 416 may be used to output any predictions output by the machine learning model 408, thus calibrating predictions made by the machine learning model 408.

After obtaining the calibration parameter 416, at sequence 404, patient characteristics 418 of a patient being treated by one of the same set of radiotherapy machines for which the machine learning model 408 was calibrated may be input into the machine learning model 408. The patient characteristics 418 may include values of the same attributes or characteristics as the patient characteristics of the calibration characteristics 406. The machine learning model 408 may receive the patient characteristics 418 and output a treatment attribute prediction 420 including one or more confidence scores for different treatment attributes (e.g., field geometry settings). The computer may input the treatment attribute prediction 420 into a prediction adjuster 422 with the previously determined calibration parameter 416. The prediction adjuster 422 may comprise instructions executable by one or more processors that causes the processors to perform one or more operations on the treatment attribute prediction 420 using the calibration parameter 416 to output a calibrated treatment attribute prediction 424 including calibrated confidence scores of treatment attribute prediction 420 output by the machine learning model 408.

The computer may obtain the calibrated treatment attribute prediction 424 and perform several actions using the prediction. For example, the computer may be connected to a radiotherapy machine of the set of radiotherapy machines and the treatment attribute prediction 424 may include confidence scores for different field geometry settings. The computer may compare the confidence scores of the calibrated treatment attribute prediction 424 to a threshold (e.g., a predetermined threshold). Responsive to identifying a confidence score that exceeds the threshold, the computer may identify the field geometry setting associated with the confidence score that exceeds the threshold and adjust or operate the radiotherapy machine to treat the patient using the field geometry setting. In another example, the computer may display the one or more confidence scores and associated field geometry settings to a user such as the patient, a doctor, or a clinician. The user may either agree with the prediction and provide an input that causes the radiotherapy machine to adjust its configuration according to the displayed setting or provide an input rejecting the displayed setting. Such may be advantageous when the machine learning model 408 is not confident above a threshold about a specific treatment (e.g., the system may display the setting responsive to determining the calibrated confidence score does not exceed a threshold) or if a patient is more comfortable making decisions themselves rather than relying on a computer.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:
    retrieving, by one or more processors via a radiation therapy treatment generation (RTTP) model, a set of treatment attribute predictions for a radiotherapy treatment of a patient;
    executing, by the one or more processors, a calibration model using the set of treatment attribute predictions and a set of labels indicating expected treatment attribute predictions to predict a calibration value; and
    revising, by the one or more processors, at least one configuration of the RTTP model using the calibration value.

2. The method of claim 1, further comprising:
    responsive to revising the at least one configuration of the RTTP model, executing, by the one or more processors, the calibration model to predict a second calibration value.

3. The method of claim 1, wherein the RTTP model is initially partially trained and then calibrated using the calibration model.

4. The method of claim 1, wherein the calibration value corresponds to a clinic, such that the RTTP model is trained for the clinic.

5. The method of claim 1, further comprising:
    adjusting, by the one or more processors, a configuration of a radiotherapy machine according to at least one treatment attribute prediction generated by the RTTP model.

6. The method of claim 1, wherein the calibration model is one of a machine learning model or a mathematical optimization algorithm.

7. The method of claim 1, further comprising:
    generating, by the one or more processors, a confidence score for the set of treatment attribute predictions generated using the RTTP model.

8. The method of claim 1, wherein at least one treatment attribute prediction within the set of treatment attribute predictions is an angle associated with a couch or a gantry of a radiotherapy machine.

9. A system comprising:
    at least one processor;
    a computer readable medium comprising a set of instructions, that when executed, cause the at least one processor to:
        retrieve, via a radiation therapy treatment generation (RTTP) model, a set of treatment attribute predictions for a radiotherapy treatment of a patient;
        execute a calibration model using the set of treatment attribute predictions and a set of labels indicating expected treatment attribute predictions to predict a calibration value; and
        revise at least one configuration of the RTTP model using the calibration value.

10. The system of claim 9, wherein the set of instructions further cause the at least one processor to:
    responsive to revising the at least one configuration of the RTTP model, execute the calibration model to predict a second calibration value.

11. The system of claim 9, wherein the RTTP model is initially partially trained and then calibrated using the calibration model.

12. The system of claim 9, wherein the calibration value corresponds to a clinic, such that the RTTP model is trained for the clinic.

13. The system of claim 9, wherein the set of instructions further cause the at least one processor to:
    adjust a configuration of a radiotherapy machine according to at least one treatment attribute prediction generated by the RTTP model.

14. The system of claim 9, wherein the calibration model is one of a machine learning model or a mathematical optimization algorithm.

15. The system of claim 9, wherein the set of instructions further cause the at least one processor to:
    generate a confidence score for the set of treatment attribute predictions generated using the RTTP model.

16. The system of claim 9, wherein at least one treatment attribute prediction within the set of treatment attribute predictions is an angle associated with a couch or a gantry of a radiotherapy machine.

17. A system comprising:
 a radiation therapy treatment generation (RTTP) model;
 a calibration model;
 a server in communication with the RTTP model and the calibration model, the server configured to:
  retrieve, via the RTTP model, a set of treatment attribute predictions for a radiotherapy treatment of a patient;
  execute the calibration model using the set of treatment attribute predictions and a set of labels indicating expected treatment attribute predictions to predict a calibration value; and
  revise at least one configuration of the RTTP model using the calibration value.

18. The system of claim 17, wherein the server is further configured to:
 responsive to revising the at least one configuration of the RTTP model, execute the calibration model to predict a second calibration value.

19. The system of claim 17, wherein the RTTP model is initially partially trained and then calibrated using the calibration model.

20. The system of claim 17, wherein the calibration value corresponds to a clinic, such that the RTTP model is trained for the clinic.

\* \* \* \* \*